United States Patent [19]

Cotterrell

[11] 3,935,212
[45] Jan. 27, 1976

[54] PESTICIDAL SUBSTITUTED 2-HYDROXYLAMINOPYRIMIDINYL PHOSPHORUS ESTERS

[75] Inventor: Graham Paul Cotterrell, Wokingham, England

[73] Assignee: Imperial Chemical Industries Limited, London, England

[22] Filed: Nov. 19, 1973

[21] Appl. No.: 417,088

[30] Foreign Application Priority Data
Dec. 18, 1972 United Kingdom............... 58290/72

[52] U.S. Cl. 260/256.4 E; 260/251 P; 260/256.5 R; 424/200
[51] Int. Cl.$^2$........................................ C07D 239/46
[58] Field of Search.... 260/256.4 E, 251 P, 256.5 R

[56] References Cited
UNITED STATES PATENTS

| | | | |
|---|---|---|---|
| 3,657,247 | 4/1972 | Freeman et al. | 260/256.4 E |
| 3,663,544 | 5/1972 | Milzner et al. | 260/256.4 E |

FOREIGN PATENTS OR APPLICATIONS

| | | | |
|---|---|---|---|
| 1,129,797 | 10/1968 | United Kingdom | 260/256.4 E |
| 1,129,563 | 10/1968 | United Kingdom | 260/256.4 E |
| 1,203,026 | 8/1970 | United Kingdom | 260/256.4 E |

*Primary Examiner*—Paul M. Coughlan, Jr.
*Attorney, Agent, or Firm*—Cushman, Darby & Cushman

[57] ABSTRACT

Compounds such as o,o-diethyl O(4-methyl-2-[N-methyl-N-methoxyamino]pyrimidin-6-yl) phosphorothioate are prepared and tested against a variety of insect and other invertebrate pests.

6 Claims, No Drawings

PESTICIDAL SUBSTITUTED 2-HYDROXYLAMINOPYRIMIDINYL PHOSPHORUS ESTERS

This invention relates to hydroxylamine derivatives, their preparation, compositions comprising them, and methods of using them to combat pests.

Accordingly the present invention provides new compounds having the formula:

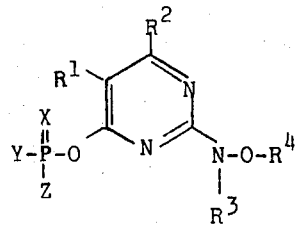

or an acid-addition salt thereof, wherein X is oxygen or sulphur; Y and Z which may be the same or different are alkyl, alkoxy, amino, alkylamino, dialkylamino or phenyl; $R^1$ and $R^2$ which may be the same or different are hydrogen, halogen, alkyl or alkoxy; $R^3$ is hydrogen, alkyl or acyl; and $R^4$ is alkyl.

Preferably X is oxygen or sulphur; Y and Z which may be the same or different are lower alkoxy or lower alkylamino; $R^1$ is hydrogen; $R^2$ is lower alkyl; $R^4$ is alkyl of 1 to 10 carbon atoms; and $R^3$ is hydrogen, lower alkyl, or lower carboxylic acyl.

Especially preferred compounds are those in which X is oxygen or sulphur; Y and Z which may be the same or different are methoxy, ethoxy, or methylamino; $R^1$ is hydrogen; $R^2$ is methyl; $R^3$ is hydrogen, methyl, ethyl or acetyl; and $R^4$ is methyl, ethyl or n-decyl.

Particular compounds include those listed in Table I below, wherein the meanings of X, Y, Z, $R^1$, $R^2$, $R^3$ and $R^4$ are given together with a physical characteristic for each compound.

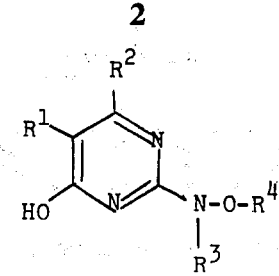

or an alkali metal salt thereof, with a compound of formula:

wherein Q is halogen, and X, Y, Z, $R^1$, $R^2$, $R^3$ and $R^4$ have any of the meanings given hereinabove, the process optionally taking place in the presence of a non-reacting diluent or solvent and/or a base. Preferred alkali metal salts are sodium and potassium salts, and a preferred meaning of Q is chlorine.

The process may take place at a temperature within the range 15°–150°C but preferably within the range 50°–100°C.

In another aspect the invention also provides, as intermediates in the preparation of the phosphorylated invention compounds hereinabove defined, new compounds of formula:

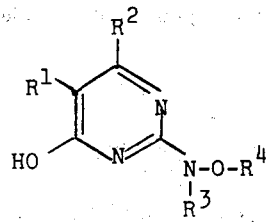

wherein $R^1$ and $R^2$ which may be the same or different

TABLE I

| Compound No | X | Y | Z | $R^1$ | $R^2$ | $R^3$ | $R^4$ | Physical Characteristic |
|---|---|---|---|---|---|---|---|---|
| 1 | S | $OC_2H_5$ | $OC_2H_5$ | H | $CH_3$ | $CH_3$ | $CH_3$ | $n_D^{25}$ 1.5161 |
| 2 | S | $OC_2H_5$ | $OC_2H_5$ | H | $CH_3$ | H | $CH_3$ | m.p. 69–70°C |
| 3 | S | $OCH_3$ | $OCH_3$ | H | $CH_3$ | $CH_3$ | $CH_3$ | $n_D^{23}$ 1.5257 |
| 4 | S | $OC_2H_5$ | $OC_2H_5$ | H | $CH_3$ | H | $C_2H_5$ | m.p. 67–69°C |
| 5 | S | $OCH_3$ | $OCH_3$ | H | $CH_3$ | H | $C_2H_5$ | m.p. 58–61°C |
| 6 | O | $NHCH_3$ | $OCH_3$ | H | $CH_3$ | H | $C_2H_5$ | $n_D^{20}$ 1.5175 |
| 7 | S | $OC_2H_5$ | $OC_2H_5$ | H | $CH_3$ | $CH_3CO$ | $C_2H_5$ | m.p. 61–62°C |
| 8 | S | $OCH_3$ | $OCH_3$ | H | $CH_3$ | $CH_3CO$ | $C_2H_5$ | m.p. 40°C |
| 9 | S | $OC_2H_5$ | $OC_2H_5$ | H | $CH_3$ | $C_2H_5$ | $C_2H_5$ | viscous oil |
| 10 | S | $OC_2H_5$ | $OC_2H_5$ | H | $CH_3$ | H | $C_{10}H_{21}(n)$ | $n_D^{24}$ 1.5042 |

Also included within the scope of the present invention are the acid-addition salts of compounds defined hereinabove. Of particular interest are the salts formed with the hydrohalic acids, for example hydrochloric acid, with sulphuric acid, and with certain organic acids, for example oxalic acid, and paratoluenesulphonic acid.

The invention compounds as defined hereinabove (except the salts thereof) may be prepared by the process of treating a compound of formula:

are hydrogen, halogen, alkyl or alkoxy; $R^3$ is hydrogen, alkyl or acyl and $R^4$ is alkyl.

Particular intermediates include those listed in Table 2 below, wherein the meanings of $R^1$, $R^2$, $R^3$ and $R^4$ are given together with a melting point for each compound.

TABLE 2

| Intermediate No. | $R^1$ | $R^2$ | $R^3$ | $R^4$ | m.p. °C |
|---|---|---|---|---|---|
| A | H | $CH_3$ | H | $CH_3$ | 173–174 |
| B | H | $CH_3$ | $CH_3$ | $CH_3$ | 128–129 |
| C | $n-C_4H_9$ | $CH_3$ | H | $CH_3$ | 158–160 |
| D | H | $CH_3$ | H | $C_2H_5$ | 174–176 |
| E | $CH_3$ | $CH_3$ | $CH_3$ | $CH_3$ | 169–171 |

TABLE 2-continued

| Intermediate No. | R¹ | R² | R³ | R⁴ | m.p. °C |
|---|---|---|---|---|---|
| F | H | Me | H | n-C₁₀H₂₁ | 114–116 |
| G | n-C₄H₉ | Me | H | n-C₁₀H₂₁ | 73–74 |

The intermediates are prepared by treatment of a compound of formula:

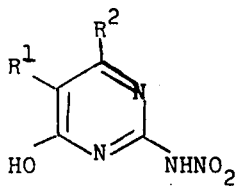

with a hydroxylamine derivative of formula:

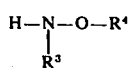

or an acid addition salt thereof, wherein R¹, R², R³ and R⁴ have any of the meanings given hereinabove, optionally in the presence of a non-reacting solvent or diluent, and optionally under a pressure greater than atmospheric pressure. A suitable solvent or diluent for this process is water or one containing a major proportion of water.

The invention compounds of formula:

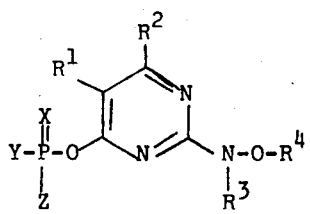

or acid salts thereof may be used to combat pests on their own, but are preferably used in the form of compositions which comprise in additin to the compound or salt thereof, a diluent material.

In a further aspect therefore the invention provides a pesticidal composition comprising as an active ingredient a compound having the formula:

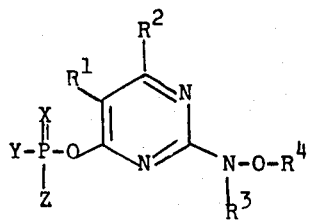

or an acid addition salt thereof, wherein X, Y, Z, R¹, R², R³ and R⁴ have any of the meanings as hereinabove defined, together with a diluent.

The compositions may be in the form of dusting powders wherein the active ingredient is mixed with a solid diluent or carrier, for example, kaolin, bentonite, kieselguhr, or talc, or they may be in the form of granules, wherein the active ingredient is absorbed on a porous granular material, for example pumice.

Alternatively the compositions may be in the form of liquid preparations to be used as dips or sprays, which are generally aqueous dispersions or emulsions of the active ingredients in the presence of one or more known wetting agents, dispersing agents or emulsifying agents. These compositions are prepared by dissolving the active ingredient in a suitable solvent, for example, a ketonic solvent such as diacetone alcohol, and adding the mixture so obtained to water which may contain one or more known wetting, dispersing or emulsifying agents.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water in order to form aqueous preparations which remain homogeneous for a sufficient time to enable them to be applied by conventional spray equipment. The concentrates may contain 10–85% by weight of the active ingredient or ingredients. When diluted to form aqueous preparations, such preparations may contain varying amounts of the active ingredient depending upon the purpose for which they are to be used.

For agricultural or horticultural purposes, an aqueous preparation containing between 0.0001% and 0.1% by weight of the active ingredient or ingredients may be used.

The compositions of the present invention may, if desired, also comprise in addition to a compound of the present invention, at least one other biologically-active ingredient, for example an insecticide, or a fungicide.

In use the compositions are applied to the pests, to the locus of the pests, to the habitat of the pests, or to growing plants liable to infestation by the pests, by any of the known means of applying pesticidal compositions, for example, by dusting or spraying.

The phosphorylated compounds of the invention and compositions comprising them are very toxic to wide varieties of insect and other invertebrate pests, including, for example, the following:

*Tetranychus telarius* (red spider mites)
*Aphis fabae*, (aphids)
*Megoura viceae* (aphids)
*Aedes aegypti* (mosquitos)
*Dysdercus fasciatus* (capsids)
*Musca domestica* (houseflies
*Blatella germanica* (cockroaches)
*Pieris brassicae* (white butterfly, larvae)
*Plutella maculipennis* (diamond back moth, larvae)
*Phaedon cochleariae* (mustard beetle)
*Calandra granaria* (grain beetle)
*Tribolium confusum* (flour beetle)

The invention is illustrated but not limited by the following examples.

EXAMPLE 1

This example illustrates the preparation of 4-hydroxy-6-methyl-2-(N-methyl-N-methoxyamino)-pyrimidine (Compound B of Table 2).

To a solution of N,O-dimethylhydroxylamine hydrochloride (7.7g) in water (40 ml) was added, firstly, sodium bicarbonate (6.5 g) and, secondly, 4-hydroxy-6-methyl-2-nitraminopyrimidine (10.8 g) and the resultant mixture was heated at 100°C for 2 hours. After filtering hot to remove traces of insoluble material the filtrate was cooled and extracted with chloroform (12 × 25 ml). The extracts were dried over anhydrous sodium sulphate and the solvent evaporated. The residual solid was recrystallised twice from benzene to yield 4-hydroxy-6-methyl-2(N-methyl-N-methoxyamino) pyrimidine having a melting point of 128°–129°C.

EXAMPLE 2

By a similar procedure to that illustrated in Example 1, but using the appropriate hydroxylamine derivative and the appropriate 2-nitraminopyrimidine, Compounds A, C, D, E, F and G of Table 2 were also prepared.

EXAMPLE 3

This example illustrates the preparation of 0,0-diethyl O(4-methyl-2-[N-methyl-N-methoxyamino]-pyrimidin-6-yl) phosphorothioate, (Compound No.1 Table I).

To a mixture of anhydrous potassium carbonate (8.8 g) and 4-hydroxy-6-methyl-2-(N-methyl-N-methoxyamino) pyrimidine (5.8 g) in dry acetone (65 ml) was added diethylphosphorothionochloridate (6.2 g). The mixture was stirred for 72 hours at the ambient temperature (ca 18°–20°C) after which the insoluble portion was removed by filtration and the filtrate evaporated under reduced pressure at the ambient temperature. The residual oil was dissolved in dichloromethane and washed with 2% w/v aqueous sodium hydroxide solution and with water. After drying the dichloromethane fraction over anhydrous sodium sulphate the solvent was removed by evaporation under reduced pressure to yield O,O,diethyl O-(4-methyl-2[-N-methyl-N-methoxyamino]pyrimidin-6-yl phosphorothionate, as an oil, $n_D^{20}$ 1.5161.

EXAMPLE 4

This example illustrates the preparation of O,O-diethyl O(4-methyl-2-N-ethoxyaminopryimidin-6-yl) phosphorothionate (Compound No. 4, Table I).

To a mixture of anhydrous potassium carbonate (9.35 g) and 2-N-ethoxyamino-4-hydroxy-6-methyl-pyrimidine (5.7 g) in dry acetone (40 ml) was added diethylphosphorothionochloridate (7.0 g) and the mixture was stirred for 60 hours at the ambient temperature, after which the insoluble material was removed by filtration. The filtrate was evaporated at the ambient temperature and the residue dissolved in dichloromethane. After washing the dichloromethane solution with 2% w/v aqueous sodium hydroxide solution and with water, and drying over anhydrous sodium sulphate, the solvent was evaporated under reduced pressure to yield a residual oil, which crystallised on trituration with petroleum ether. The solid was collected by filtration, washed with petroleum ether, and dried to yield O,O-diethyl O(4-methyl-2-N-ethoxyaminopyrimidin-6-yl phosphorothionate, having a melting point of 67°–69°C.

EXAMPLE 5

By a procedure similar to those illustrated in Examples 3 and 4, but using the appropriate phosphorus halide and the appropriate hydroxy pyrimidine, the compounds numbered 2, 3, 5 and 7 to 10 of Table I were also prepared.

EXAMPE 6

This compound illustrates the preparation of O,N-dimethyl O(4-methyl-2-[N-methyl-N-methoxyamino]-pyrimidin-6-yl) phosphoramidate (Compound No. 6 of Table I).

Sodium (0.56 g) was dissolved in ethanol (25 ml) and to the solution of sodium ethoxide thus formed was added 4-hydroxy-6-methyl-2-[N-methyl-N-methoxyamino]pyrimidine (4.2 g).

The solution was stirred for 1 hour, after which the ethanol was removed under reduced pressure to yield a residue of the sodium salt of the hydroxypyrimidine, which was freed from the final traces of ethanol by azeotropic disstillation using toluene under reduced pressure. The dry salt was suspended in toluene (50 ml) and the suspension treated over a period of 10 minutes with a solution of O,N-dimethylphosphoramido-chloridate (2.57 g) in toluene (35 ml). The resultant mixture was stirred at the ambient temperature for 1 hour and thereafter at 60°C for 3 hours. On cooling the mixture was extracted with water, and the toluene portion dried over anhydrous sodium sulphate. The solvent was evaporated under reduced pressure to yield O,N-dimethyl-O(4-methyl-2[N-methyl-N-methoxyamino]pyrimidin-6-yl) phosphoramidate as a viscous oil, $n_D^{23}$ 1.5175.

EXAMPLE 7

5 Parts by weight of Compound No. 1 of Table I were thoroughly mixed in a suitable mixer with 95 parts by weight of talc. There was thus obtained a dusting powder.

EXAMPLE 8

10 Parts by weight of Compound No. 2 Table I, 10 parts of an ethylene oxide-octylphenol condensate ("Lissapol" NX: "Lissapol" is a Trade Mark) and 80 parts by weight of diacetone alcohol were thoroughly mixed. There was thus obtained a concentrate which, in mixing with water, gave an aqueous dispersion suitable for application as a spray in the control of insect pests.

EXAMPLE 9

A granular composition was prepared by dissolving the active ingredient in a solvent, spraying the solution obtained on to the granules of pumice and allowing the solvent to evaporate.

|  | % wt. |
| --- | --- |
| Compound No.3 of Table I | 5 |
| Pumice Granules | 95 |
|  | 100% |

EXAMPLE 10

An aqueous dispersion formulation was prepared by mixing and grinding the ingredients recited below in the proportions stated.

|  | % wt. |
| --- | --- |
| Compound No.4 of Table I | 40 |
| Calcium lignosulphonate | 10 |
| Water | 50 |
|  | 100% |

EXAMPLE 11

The activity of a number of the compounds was tested against a variety of insect and other invertebrate pests. The compounds were used in the form of a liquid preparation containing 0.1% by weight of the compound except in the tests with *Aedes aeqypti* where the preparations contained 0.01% by weight of the compound. The preparations were made by dissolving each of the compounds in a mixture of solvents consisting of 4 parts of volume of acetone and 1 part by volume of diacetone alcohol. The solutions were then diluted with water containing 0.01% by weight of a wetting agent sold under the trade name LISSAPOL NX until the liquid preparations contained the required concentration of the compound. Lissapol is a Trade Mark.

The results of the tests are given below in Table 3. In this table the first column indicates the name of the pest species. Each of the subsequent columns indicates the host plant or medium on which it was supported, the number of days which were allowed to elapse after the treatment before assessing the mortality of the pests, and the results obtained for each of the compounds, numbered as in Table I above. The assessment is expressed in integers which range from 0-3.

0 represents less than 30% kill
1 represents 30-49 % kill
2 represents 50-90% kill
3 represents over 90% kill A dash in Table 3 indicates that no test was carried out.

TABLE 3

| Pest Species | Support Medium | No. days | Compound No. (Table 1) | | | | | | | | | |
|---|---|---|---|---|---|---|---|---|---|---|---|---|
| | | | 1 | 2 | 3 | 4 | 5 | 6 | 7 | 8 | 9 | 10 |
| *Tetranychus telarius* (red spider mites, adults) | French Bean | 3 | 3 | 3 | 3 | 3 | 3 | 3 | 3 | 3 | — | 3 |
| *Tetranychus telarius* (red spider mites, eggs) | French Bean | 3 | 2 | 0 | 0 | 2 | 3 | 0 | 3 | 3 | — | 0 |
| *Aphis fabae* (green aphids) | Broad Bean | 2 | 3 | 3 | 3 | 3 | 3 | 3 | 3 | 3 | — | 3 |
| *Megoura viceae* (black aphids) | Broad Bean | 2 | 3 | 3 | 3 | 3 | 3 | 3 | 3 | 3 | — | 3 |
| *Aedes aegypti* (mosquito adults) | Plywood | 1 | 3 | 2 | 3 | 0 | 0 | 3 | 3 | 0 | 3 | 3 |
| *Musca domestica* (houseflies-contact test) | Milk/sugar | 2 | 3 | 3 | 3 | 3 | 3 | 3 | 3 | 3 | 3 | 3 |
| *Musca domestica* (houseflies-residual test) | Plywood | 2 | 3 | 0 | 3 | 3 | 0 | 2 | 3 | 2 | 0 | 0 |
| *Pieris brassicae* (cabbage white caterpillars systemic test) | Cabbage | 2 | 3 | 0 | 0 | 0 | 0 | 0 | 0 | 0 | 0 | 0 |
| (*Pieris brassicae* (cabbage white caterpillars contact test) | Cabbage | 2 | 3 | 3 | 3 | 3 | 3 | 3 | 3 | 3 | 3 | 2 |
| *Dysdercus fasciatus* (cotton stainer capsid) | Grain | 2 | 3 | 0 | 3 | 0 | 3 | 3 | 3 | 0 | 0 | 3 |
| *Plutella maculipennis* (diamond back moth, larvae - systemic test) | Mustard | 2 | 3 | 0 | 3 | 0 | 0 | 0 | 0 | 1 | 2 | 0 |
| *Plutella maculipennis* (diamond back moth, larvae - contact test) | Mustard | 2 | 0 | 1 | 2 | 3 | 3 | 2 | 0 | 2 | 0 | 0 |
| *Phaedon cochleariae* (mustard beetles - residual test) | Mustard | 2 | 3 | 3 | 3 | 3 | 3 | 3 | 3 | 3 | 0 | 1 |
| *Phaedon cochleariae* (mustard beetles - systemic test) | Mustard | 2 | 1 | 3 | 3 | 0 | 3 | 3 | 3 | 2 | 0 | 0 |
| *Calandra granaria* (grain beetles) | Grain | 2 | 3 | 3 | 3 | 3 | 3 | 3 | 3 | 3 | 3 | 3 |
| *Tribolium confusum* (flour beetles) | Grain | 2 | 3 | 3 | 3 | 3 | 3 | 3 | 3 | 3 | 3 | 3 |
| *Plattella germanica* (cochroaches) | — | 1 | 3 | 3 | 3 | 3 | 3 | 3 | 3 | 3 | 3 | 2 |
| *Meloidogyne incognita* (nematodes) | Water | 1 | 0 | 3 | 0 | 0 | 0 | 0 | 0 | 0 | 0 | — |
| *Aedes aegypti* (mosquito larvae) | Water | 1 | 3 | 3 | 3 | 3 | 3 | 3 | 3 | 3 | 3 | 3 |

The test procedure adopted with regard to each pests was basically the same and comprised supporting a number of the pests on a medium which was usually a host plant or a foodstuff on which the pests feed, and treating either or both the pests and the medium with the preparations.

The mortality of the pests was then assessed at periods usually varying from one to three days after the treatment.

In the foregoing Table "contact test" indicates that both the pests and the medium were treated, "residual test" indicates that the medium was treated before infestation with the pests, and "systemic test" indicates that the leaves of the host plant were infested after the roots of the plant had been treated with the composition of the compound under test.

I claim:

1. A compound of the formula:

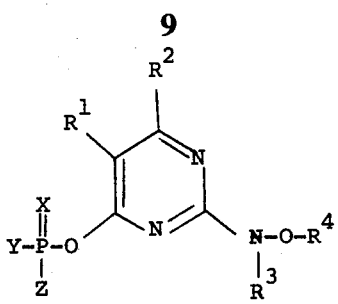

or acid-addition salt thereof, wherein X is oxygen or sulphur; Y and Z are lower alkoxy or lower alkylamino; R¹ is hydrogen; R² is lower alkyl; R⁴ is alkyl of 1 to 10 carbon atoms, and R³ is hydrogen, lower alkyl or acetyl.

2. A compound according to claim 1 wherein X is oxygen or sulphur; Y and Z which may be the same or different are methoxy, ethoxy or methylamino; R¹ is hydrogen; R² is methyl; R³ is hydrogen, methyl, ethyl or acetyl and R⁴ is methyl, ethyl or n-decyl.

3. A compound as claimed in claim 1 selected from the group of compounds consisting of:

O,O-diethyl O(4-methyl-2-[N-methyl-N-methoxyamino]pyrimidin-6-yl) phosphorothionate,
O,O-diethyl O(4-methyl-2-methoxyaminopyrimidin-6-yl) phosphorothionate
O,O-dimethyl O(4-methyl-2-[N-methyl-N-methoxyamino] pyrimidin-6-yl) phosphorothionate,
O,O-diethyl O(4-methyl-2-ethoxyaminopyrimidin-6-yl) phosphorothionate,
O,O-dimethyl O(4-methyl-2-ethoxyaminopyrimidin-6-yl) phosphorothionate, and
O,O-diethyl O(4-methyl-2[N-ethyl-N-ethoxyamino]-pyrimidin-6-yl) phosphorothionate.

4. A compound as claimed in claim 1 selected from the group of compounds consisting of:

O,O-diethyl O(4-methyl-2-N-ethoxyacetamidopyrimidin-6-yl)phosphorothionate, and
O,O-dimethyl O(4-methyl-2-N-ethhoxyacetamidopyrimidin-6-yl) phosphorothionate.

5. O,O-diethyl O(4-methyl-2-n-decyloxyaminopyrimidin-6-yl) phosphorothionate.

6. O,N-dimethyl O(4-methyl-2[N-methyl-N-methoxyamino]-pyrimidin-6-yl) phosphoramidate.

* * * * *